(12) United States Patent
Hill

(10) Patent No.: US 6,352,546 B1
(45) Date of Patent: Mar. 5, 2002

(54) TATTOO NEEDLE PNEUMATIC OPERATING MECHANISM

(76) Inventor: Carson F. Hill, 726 Paseo Montecito, Newbury Park, CA (US) 91320

(*) Notice: Subject to any disclaimer, the term of this patent is extended or adjusted under 35 U.S.C. 154(b) by 17 days.

(21) Appl. No.: 09/715,608

(22) Filed: Nov. 20, 2000

(51) Int. Cl.[7] .................................. A61B 17/34

(52) U.S. Cl. ...................... 606/186; 415/904

(58) Field of Search ................................ 606/186, 184, 606/185, 187, 188, 189, 1; 604/46, 47, 48; 81/9.22, 9.21; 415/202, 904, 191, 140, 141; 433/132, 126, 129

(56) References Cited

U.S. PATENT DOCUMENTS

| 3,955,284 A | * | 5/1976 | Balson ........................ 415/904 |
| 4,204,438 A | * | 5/1980 | Binaris et al. ................ 81/9.22 |
| 6,033,421 A | * | 3/2000 | Theiss et al. ................ 606/186 |

* cited by examiner

*Primary Examiner*—Kevin Truong
(74) *Attorney, Agent, or Firm*—Jack C. Munro

(57) ABSTRACT

A tattoo needle pneumatic operating mechanism which utilizes a housing which has an internal cavity. A fan gear is rotatably mounted within the cavity. A cam is attached to the fan gear. Mounted on the cam is a cam lobe. The cam lobe is to engage with a cam surface which is mounted in conjunction with a slide. A tattoo needle is mounted to the slide. Revolving of the fan gear by air pressure causes the slide to reciprocate which causes the needle to reciprocate.

4 Claims, 2 Drawing Sheets

TATTOO NEEDLE PNEUMATIC OPERATING MECHANISM

BACKGROUND OF THE INVENTION

1. Field of the Invention

The field of this invention relates to reciprocating or oscillating mechanisms and more particularly to a mechanism that is to be operated by air pressure and used to cause oscillation of a tattoo needle.

2. Description of the Related Art

In the forming of a tattoo on skin, a needle is utilized which includes a small quantity of ink. The needle is penetrated within the skin leaving a small spot of the ink which will result in the production of the discoloration of the skin. Repeating this procedure numerous times in a particular pattern with different colors of ink in conjunction with the tattoo needle will result in the production of the desired tattoo.

In the producing of most tattoos, it is required to insert the needle within the skin hundreds of times, and in some tattoos, even thousands of times. The most common technique of producing a tattoo is to manually insert and withdraw the needle each and every time. In order to decrease the amount of time it takes to make a tattoo, in the past it has been known to use some kind of a mechanism that causes the needle to oscillate rapidly with the user only being required to carefully move the needle from one location to another. These locations are generally adjacent to each other, and the needle will be moved continually from these locations until the desired pattern of the tattoo is reproduced. In the past, this type of mechanism has been operated electrically.

The electrical type of mechanism for causing oscillation of a tattoo needle has been rather complex and therefore inherently expensive and is readily subject to failure after a length of time of operation. It is desirable that the mechanism operate for an extended length of time without failure. It seems that the electrically operated mechanism is readily subject to failure after a certain length of time.

SUMMARY OF THE INVENTION

One of the primary objectives of the present invention is to construct a tattoo needle oscillation mechanism which can be operated over an extended length of time practically eliminating the possibility of failure.

Another objective of the present invention is to construct a tattoo needle oscillation mechanism which is composed of few parts therefore non-complex and can be manufactured at a reasonable cost and therefore sold to the ultimate consumer at a reasonable cost.

The tattoo needle pneumatic operating mechanism of the present invention utilizes a block type of housing within which is formed a cavity and an air passage. The air passage is to be connected to a source of pressurized air. A fan gear is mounted within the cavity with the fan gear being rotatable relative to the housing. A spindle is attached to the fan gear and extends upwardly therefrom. Mounted on the spindle is a cam. Mounted against the housing is a slide with there being a hole formed in the slide. The cam is located within the hole. A shaft is also mounted on the slide with a tattoo needle to be connected to the shaft. Rotation of the fan gear causes the cam to move back and forth within the hole formed within the slide which causes the slide to reciprocate (oscillate) and simultaneously the tattoo needle to also reciprocate.

BRIEF DESCRIPTION OF THE DRAWINGS

For a better understanding of the present invention, reference is to be made to the accompanying drawings. It is to be understood that the present invention is not limited to the precise arrangement shown in the drawings.

DETAILED DESCRIPTION OF THE PREFERRED EMBODIMENT

Figure 1:
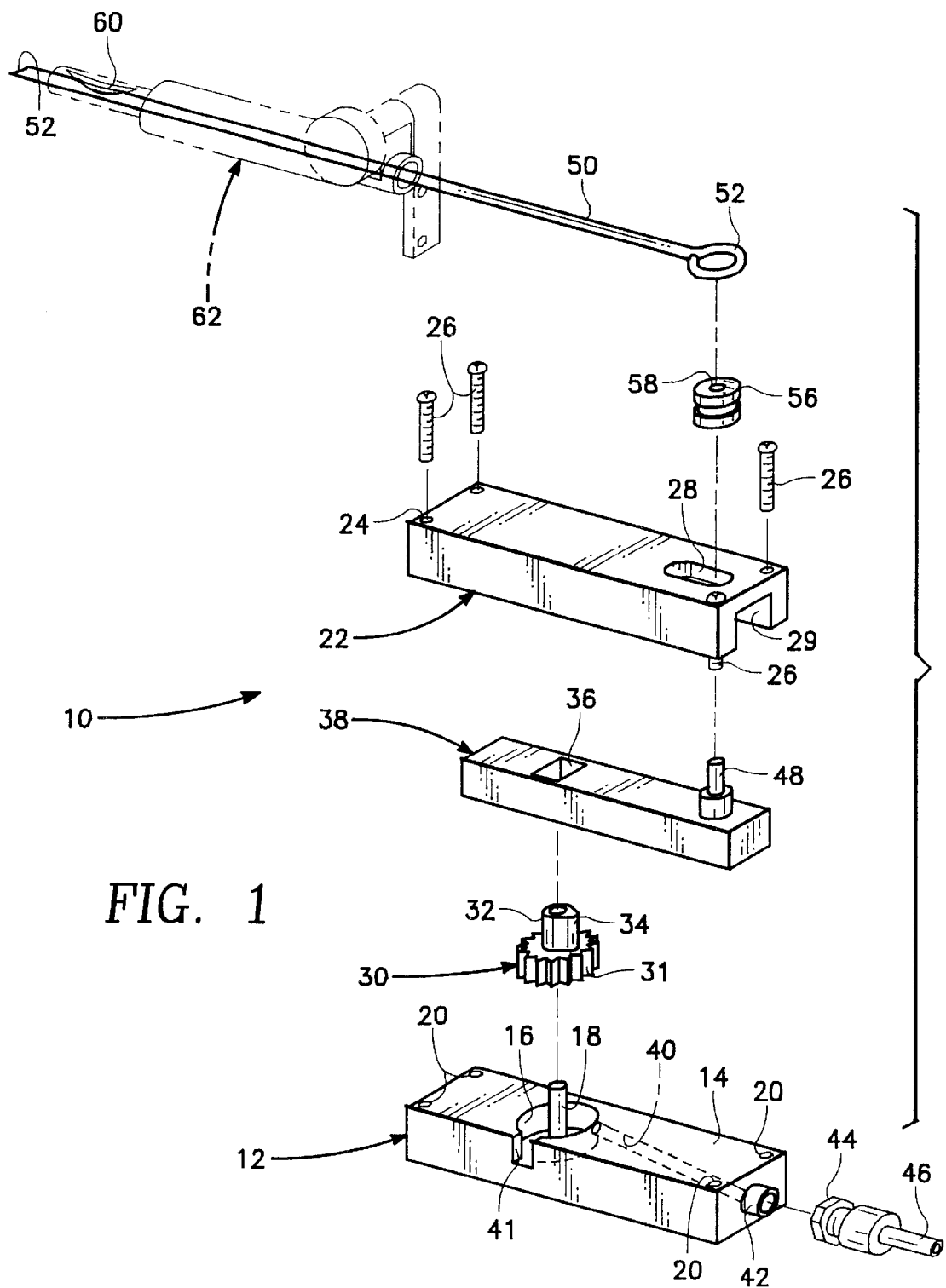
FIG. 1 is an exploded isometric view of the tattoo needle pneumatic operating mechanism of the present invention.

Referring particularly to the drawings, there is shown the tattoo needle pneumatic operating mechanism 10 of this invention. The mechanism 10 utilizes a housing 12 which is basically in the form of a rectangularly shaped block. The housing 12 has an interior planar surface 14. Formed within the planar surface 14 and within the housing 12 is a circular shaped cavity 16. Fixedly mounted within the housing 12 and centrally located within the cavity 16 is a pin 18. Typically, the pin 18 will be constructed of a metallic material with generally the housing 12 being constructed of a plastic material. Also formed within the interior surface 14 at the corners thereof are threaded holes 20 with it being understood that there are four in number of the threaded holes 20. A cover 22 is to be located on the interior surface 14. The cover 22 includes a series of holes 24 located with there being a hole at each corner thereof. A threaded screw fastener 26 is to pass through each hole 24 and threadably connect with a hole 20 thereby securely mounting the cover 22 onto the housing 12. The cover 22 includes an elongated opening 28 which connects to an elongated through channel 29.

Mounted on the pin 18 is a fan gear 30 which has a plurality of blades 31. Fixedly attached to the fan gear and extending upwardly therefrom is a cam 32. Integrally formed in conjunction with the cam 32 is a lateral protuberance which is defined as a cam lobe 34. The cam 32 and the cam lobe 34 is to connect with a rectangularly shaped hole 36 which is formed within a slide 38. The slide 38 constitutes a block of material with generally plastic being preferred. It is to be understood also that the cover 22 would generally be constructed of plastic. However, it would be within the scope of this invention the cover 22, the slide 38 and the housing 12 could also be constructed of a metallic material.

Also formed interiorly of the housing 12 is an air inlet passage 40. One end of this air inlet passage 40 connects with the cavity 16, and the opposite end of the air inlet passage 40 connects with a threaded nipple 42 that is fixedly mounted on the exterior surface of the housing 12. The threaded nipple 42 is to facilitate airtight connection with a connector 44. The connector 44 is mounted at the outer end of a flexible tube 46. The flexible tube 46 is to be connected to a source of pressurized air, which is not shown. The passage 40 is canted relative to the longitudinal center axis of the housing 12 so the passage connects to the cavity 16 almost tangentially. The reason for this is so the pressurized air will be directed against the blades 31 of the fan gear 30 and cause such to rotate. The expended air is to be discharged through slot 41 formed in the housing 12 which connects with cavity 16.

Fixedly mounted on the slide 38 is a shaft 48. The shaft 48 extends through the elongated opening 28. A tattoo needle 50 has a sharp pointed outer end 52 and a ring shaped at end 52. Mounted within the ring shaped aft end 54 is a resilient grommet 56 which is normally constructed of rubber. The shaft 48 is to be mounted within the through hole 58 formed within the grommet 56.

Figure 2:
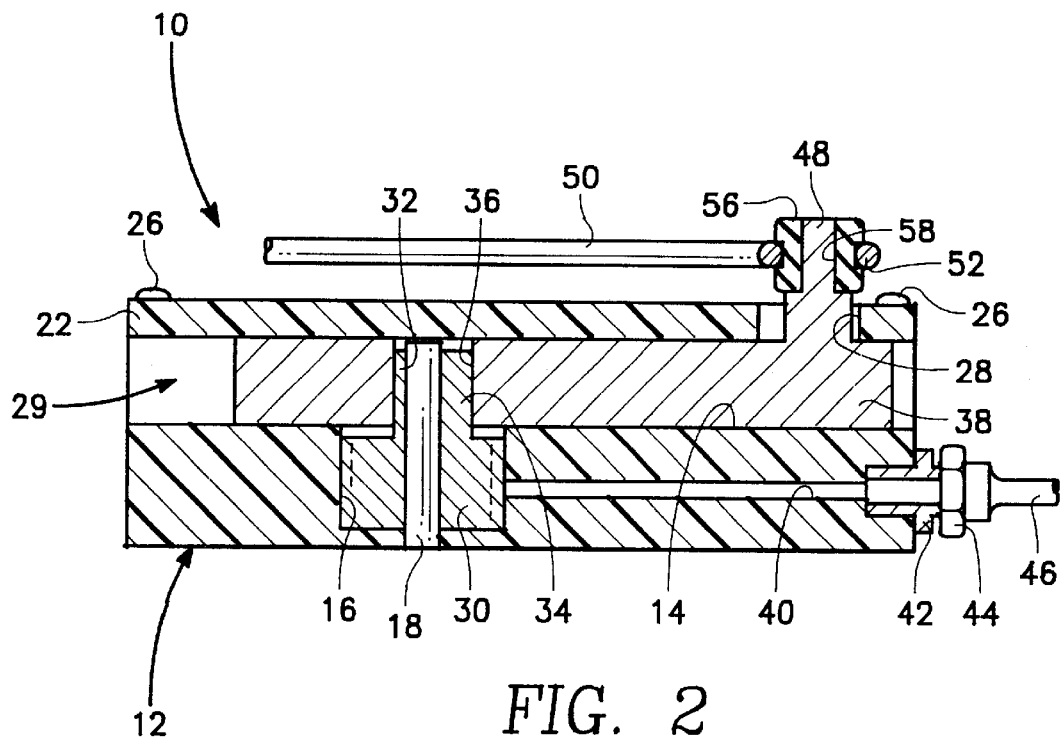
FIG. 2 is a cross-sectional view of the tattoo needle pneumatic operating mechanism of the present invention showing the mechanism in its assembled state and with the tattoo needle being in its right most position during its movement.
Figure 3:
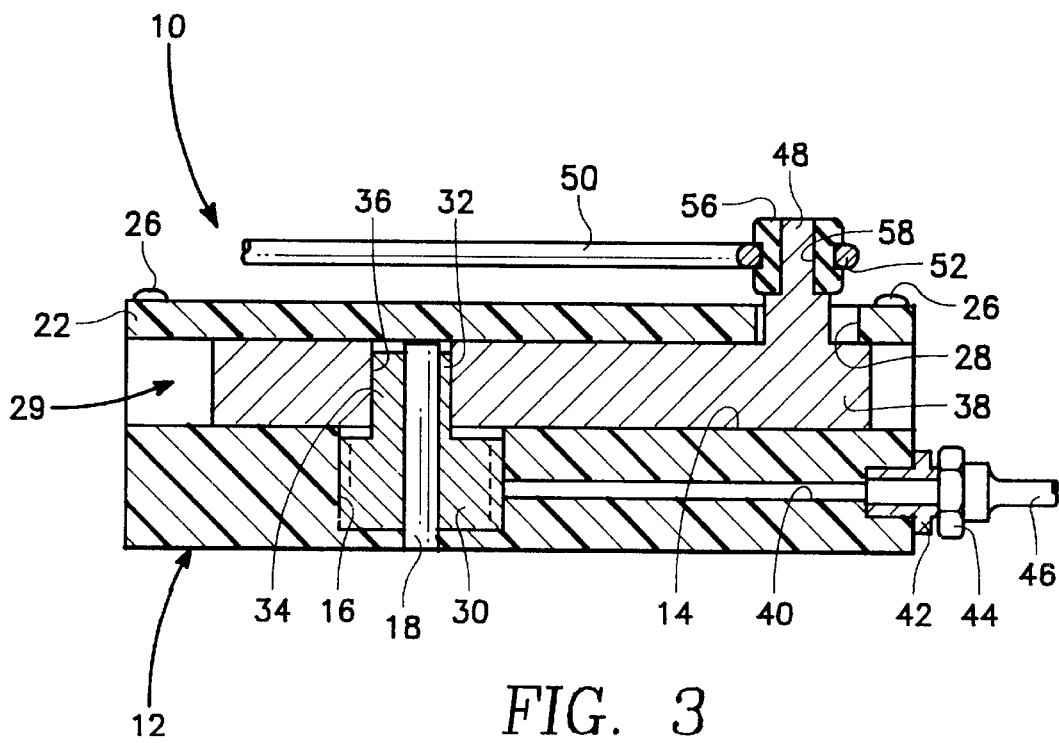
FIG. 3 is a view similar to FIG. 2 but showing the tattoo needle in its left most position in its path of movement.

The operation of the mechanism 10 of this invention is as follows: Air pressure is supplied through the tube 46 into passage 40 which is then forced against the blades 31 of the fan gear 30. As a result, the fan gear 30 is rotated which similarly rotates the cam lobe 34. The cam lobe 34 pushes against the cam surface which comprises the forward end and the rearward end of the hole 36. The result is that the slide 38 is moved between the aft position, shown in FIG. 2, and the fore position, shown in FIG. 3 with this movement continuing very rapidly, with the reciprocating movement resembling oscillations. This oscillatory movement is transferred through the shaft 48 to the tattoo needle 50 with the result that the sharp pointed outer end 52 rapidly penetrates a person's skin and then withdraws from the person's skin and then repenetrates the skin, and so forth. Ink is to be supplied to the internal cavity 60 of the needle 50. The needle 50 will generally be mounted within some type of a handle 62 with it being understood that the needle 50 is designed to reciprocate relative to the handle 62. The tattoo needle will generally be constructed of a steel that is capable of being sterilized.

The present invention may be embodied in other specific forms without departing from the essential attributes thereof. Reference should be made to the appending claims rather than the foregoing specification as indicating the scope of the invention.

What is claimed is:

1. A tattoo needle pneumatic operating mechanism comprising:

a housing having a cavity, said housing having an air passage, said air passage adapted to connect to a source of pressurized air, said air passage connecting with said cavity;

a fan gear mounted in said cavity, said fan gear capable of rotative movement;

a cam attached to said fan gear and extending therefrom;

a cam lobe attached to said cam, said cam lobe being off center relative to said cam;

a slide having a cam surface, said cam lobe to connect with said cam surface; and a needle mounting shaft mounted on said slide, said shaft adapted to connect with a tattoo needle, wherein applying of air pressure into said cavity causes said fan gear to rotate which by said cam lobe causes said slide to reciprocate which simultaneously causes said needle mounting shaft to reciprocate.

2. The tattoo needle pneumatic operating mechanism as defined in claim 1 wherein:

said cam surface comprising a non-circular hole.

3. The tattoo needle pneumatic operating mechanism as defined in claim 1 wherein:

a pin extending through said cavity and being fixedly attached to said housing, said fan gear being rotatably mounted on said pin.

4. The tattoo needle pneumatic operating mechanism as defined in claim 1 wherein:

a cover mounted on said housing, said cover having a through channel, said slide being movably mounted in said through channel.

* * * * *